United States Patent [19]
Porteous

[11] Patent Number: 5,180,374
[45] Date of Patent: Jan. 19, 1993

[54] SAFETY NEEDLE CONTAINMENT

[76] Inventor: Paul Porteous, 735 Terrace View Pl., Port Hueneme, Calif. 93041

[21] Appl. No.: 817,538

[22] Filed: Jan. 7, 1992

[51] Int. Cl.⁵ .............................................. A61M 5/32
[52] U.S. Cl. ..................................... 604/192; 604/263
[58] Field of Search ........................ 604/263, 192, 187

[56] References Cited
U.S. PATENT DOCUMENTS 4,559,042  12/1985  Votel ............................... 604/263 X
4,573,975   3/1986  Frist et al. ....................... 604/263 X Primary Examiner—John D. Yasko
Attorney, Agent, or Firm—Louis J. Bachand

[57] ABSTRACT

Safety needle containment comprises a disc shaped deflector flange projecting from the needle enclosing sheath, which may flex to and from the sheath between storage and protective positions by flexing the adjacent sheath wall.

12 Claims, 1 Drawing Sheet

— 5,180,374 —

SAFETY NEEDLE CONTAINMENT

TECHNICAL FIELD

This invention has to do with safe containment of needles and protection against inadvertent needle pricks and punctures such as may occur to medical personnel involved with the administration of medicaments. More particularly the invention is concerned with a safety needle containment by having a disc arranged on a needle sheath so as to block pricks and punctures from happening upon careless misinsertion of the used needle into its enclosing sheath.

BACKGROUND

Medical professionals are repeatedly called upon to administer medications subcutaneously to patients. Typically, the medicament is administered by a needle which has been connected to the supply from a sterile containment arrangement comprising a sheath and a cap which holds the needle for connection and which is used to dispose of the used needle safely. Numerous medicaments are put up in small, premeasured quantities in disposable syringes. These syringes typically comprise a barrel containing the medicament, and a plunger movable through the barrel to dispense the medicament. A needle structure comprising a hub with a first needle to one side and a second needle to the other side is coupled to the syringe by breaking the syringe seal with the second needle. The first needle is used to deliver the medicament to the patient.

Needles typically are provided with a sleeve or sheath which encloses the needle to avoid contamination before use and to provide a means of disposal without leaving an exposed needle after use. Sheaths are usually molded of suitable plastic and at their inner end overfit the needle structure hub securely in a firm friction fit enclosing the first needle. A cap is used to cover the second needle, the cap interfitting the sheath to form a complete enclosure of the needle structure.

When withdrawing the needle from its sheath and when reinserting the needle point first into the sheath extreme care must be taken to avoid contact of the needle point with the hands and fingers. The usual mode of insertion, however, is to grip the needle structure itself or the syringe or other attachment to the needle with one hand and to hold the sheath with the other hand. In this manner the fingers on the sheath, typically thumb and forefinger, are in jeopardy of being stuck by the needle point if the needle insertion into the sheath is off target by even a very small distance.

In these times of highly infectious, even deadly diseases being rampant in care centers, and the great speed with which medical care is necessarily being given in overcrowded facilities, the need to protect the caregiver, and others in the facility is clear.

SUMMARY OF THE INVENTION

It is an object therefore to provide an improved protection system for needles so as to block injury to the user, and possible infection, where the reinsertion of the needle is awry. It is another object to provide a modified form of needle sheath having protection means integrated into the sheath construction so as to block inadvertent punctures of the operator's skin. It is a particular object to provide a novel form of sheath in which a disc flange on the sheath guards the operator's fingers from misdirected needle exposure. Yet another object is to provide such protection in a form which fits closely to the sheath when not in use, and which snaps into a use position readily.

These and other objects of the invention to become apparent hereinafter are realized in a safety needle containment for a needle structure comprising a hub and a projecting needle, the containment comprising a needle sheath normally covering the needle before and after use, the sheath comprising a tubular element sized to enclose the needle and having a wall adapted to be gripped by fingers at a locus midway along its length for withdrawal and insertion of the needle, and a disc element mounted transversely on the sheath tubular element above the locus, the disc element being resistant to needle penetration and projecting laterally of the sheath tubular element a distance to block the needle from reaching said fingers gripping the sheath tubular element below the disc.

In this and like embodiments, typically, the sheath tubular element comprises rigid synthetic organic plastic; the disc element comprises rigid synthetic organic plastic; and there is further included cooperating structure on the needle structure hub and the sheath tubular element for removably interfitting the hub and the sheath tubular element in needle enclosing relation.

In particularly preferred embodiments, the disc element is locally flexible adjacent the sheath tubular element for alignment transverse to or parallel with the sheath tubular element wall between protective and storage positions respectively. Typically, the disc element is centrally apertured and fixed to the sheath tubular element wall at its central aperture. The disc element may integrally formed with the sheath tubular element wall.

In a further embodiment, the disc element defines an over-center structure adapted to snap between parallel and transverse positions relative to the sheath tubular element responsive to flexing of the sheath tubular element wall below the disc element.

In this and like embodiments the sheath tubular element comprises rigid synthetic organic plastic, and needle structure comprises a hub having a first needle extending from one side and a second needle extending from the opposite side, the hub being adapted to snugly interfit with the sheath tubular element, and the invention also includes a cap adapted to completely enclose the needle structure in cooperation with the sheath. As in previous embodiments, and typically, the disc element comprises rigid synthetic organic plastic, and the needle structure hub may be internally threaded for mounting a medicament supply to the needle structure.

The invention further contemplates in combination: a syringe comprising a rigid plastic barrel having a plunger and a needle outlet arranged for delivery of medicament; a needle structure including a first needle for administering medicament and a second needle for piercing the syringe barrel needle outlet, the first and second needles extending oppositely from a common hub; and a sheath forming a needle protective enclosure, the sheath having a disc element flange formed thereon to deflect the first needle from fingers gripping the sheath during insertion of the first needle into the sheath.

In this embodiment, preferably the disc element is coupled to the sheath in a manner to flex into and out of more relatively parallel alignment with the sheath responsive to lateral flexing of the sheath for storage or protective deployment respectively of the disc element.

THE DRAWINGS

The invention will be further described in conjunction with the attached drawings in which.

DETAILED DESCRIPTION

Figure 1:
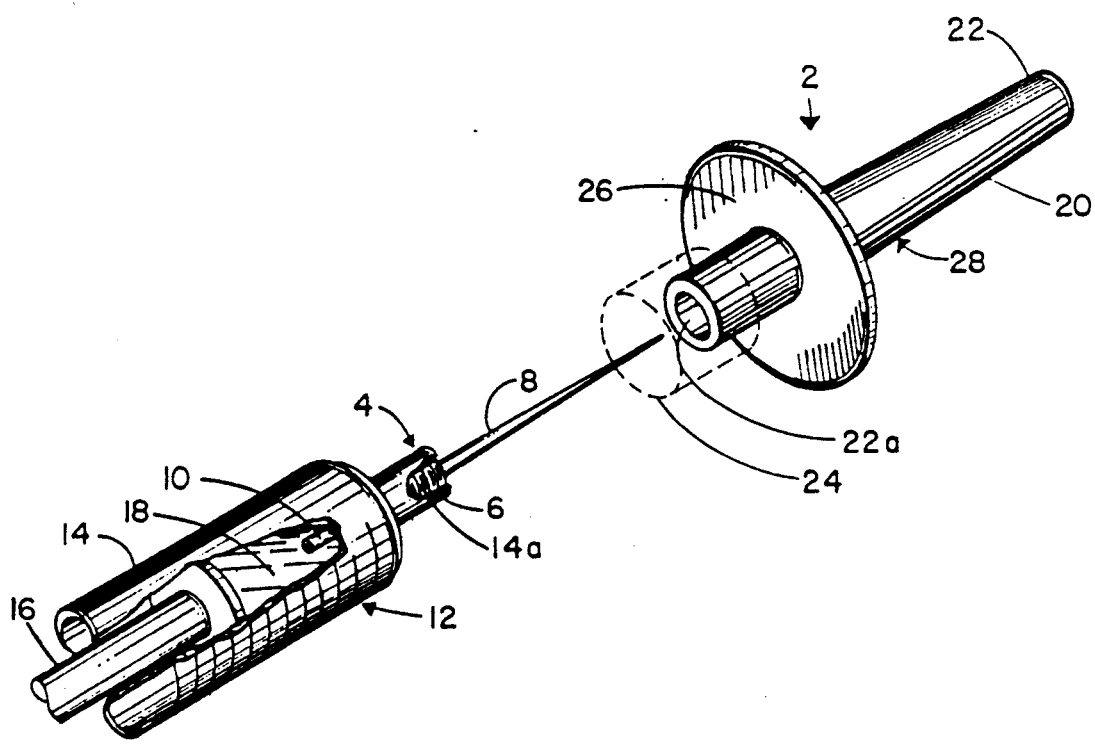
FIG. 1 is an isometric view of the safety needle containment according to the invention.
Figure 2:
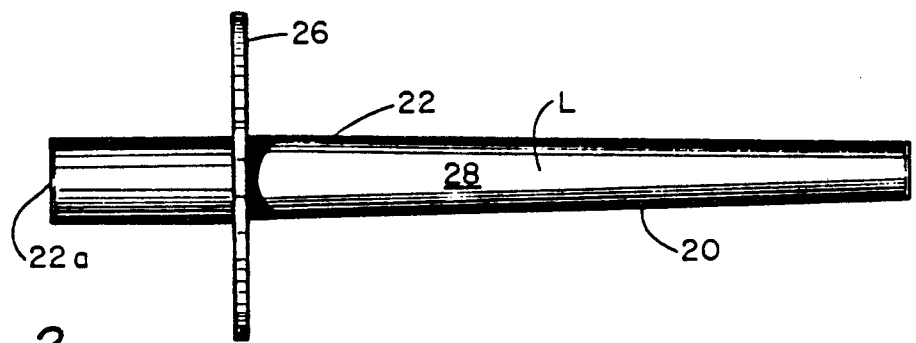
FIG. 2 is a side elevational view of the sheath portion thereof with an immovable disc element; and, FIG. 3 is a view like FIG. 2 of the sheath portion, with an flexible disc element flexed upwardly.

With reference now to the drawings, in FIGS. 1 and 2 the invention safety needle containment device is shown at 2, separated from needle structure 4 comprising a hub 6, first needle 8 for administering medicament, and second needle 10 which is used to pierce the seal of the syringe 12. Syringe 12 comprises a tubular barrel 14, suitably formed of a rigid synthetic organic plastic such as an ethylene or propylene polymer or copolymer, or a styrene or amide polymer which is resistant to medicaments to be applied therefrom and sufficiently stiff to permit injections to be made therewith. The barrel 14 terminates in an externally threaded barrel tip 14a onto which the hub 6 is screwed as the second needle 10 penetrates the syringe seal (not shown). The syringe 12 further comprises a plunger 16 adapted to slide within the barrel 14 to deliver the medicament 18 to the internally hollow second needle 10 for passage through the hub 6 and the first needle 8 for administration to a patient.

The safety needle containment 2 comprises a first needle enclosure in the form of a sheath 20 comprising a tubular element 22 sized in length and interior diameter to enclose the first needle 8. A cap 24, shown in phantom only in FIG. 1, completes the enclosure of the needle structure 4 when in place fitted over the open end 22a of sheath 20.

Sheath tubular element 22 is normally installed over the needle 8 before use and after use. The materials of construction of the sheath tubular element 22 (and the cap 24) are rigid plastic like those of the syringe barrel 14, and designed in a wall thickness to permit flexing as described below. The open end 22a of sheath tubular element 22 is further sized to snugly overfit the hub 6 so as to mount the sheath 20 to the hub when the first needle 8 is enclosed therein.

The sheath tubular element 22 has fixed to its upper bodily extent a disc element 26, a flat, centrally apertured washer-like body which can be integrally formed with the sheath tubular element 22 or separately formed and then fixed to the tubular element by heat fusion or solvent as appropriate for the materials used.

The disc element 26 is designed and manufactured to be sufficiently rigid to be impenetrable by the needle 8 if struck by the needle during an attempt to put the needle into the sheath 20, and is sized to project outwardly sufficiently to protect fingers holding the sheath midway along its length.

The disc element 26 is suitably coupled to the sheath tubular element 22 so as to be convertible to a storage mode for packing, shipping and like non-use events, but projectable outward instantly when needed. In fact, it is desirable to have the disc element 26 project outward from a storage position in response to squeezing the wall 28 of the sheath tubular element 22 at locations associated with normal gripping of the sheath 20.

Figure 3:
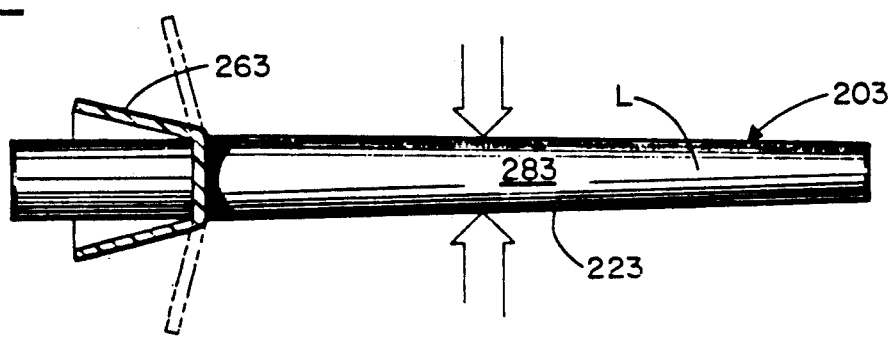

With reference to FIG. 3, a foldable form of the disc protection is shown. The disc element 263 is upwardly dished and shown connected to sheath tubular element 223 above the midpoint of the sheath tubular element. As shown by the arrows, located at the usual locus L for finger placement when gripping the sheath 203, pressure inward on the tubular element wall 283, flexes the wall inward causing the disc element 263 to snap in an over-center movement from its transverse deployment (dotted line) relative to the sheath 203 to a position parallel, or more nearly so, with the sheath. If desired the disc element 263 can be arranged to snap down rather than up, in either case coming into the tubular element 223 to reduce size of the sheath 20 for packing, shipping or storing. For use, the tubular element 223 is squeezed and the disc element 263 snaps back out to protect against inadvertent pricks and punctures by deflecting the needle 8 outward and away from fingers gripping the sheath 203 in the locus L suggested by the pressure arrows shown in FIG. 3.

The foregoing objects are thus achieved, including provision of an improved protection system for needles so as to block injury to the user, and possible infection, where the reinsertion of the needle is awry, provision of a modified form of needle sheath having protection means integrated into the sheath construction so as to block inadvertent punctures of the operator's skin, and in particular provision of a novel form of needle sheath in which a disc flange on the sheath guards the operator's fingers from misdirected needle exposure, suitably in a form which fits closely to the sheath when not in use, and which snaps into a use position readily.

I claim:

1. Safety needle containment for a needle structure comprising a hub and a projecting needle, said containment comprising a needle sheath normally covering the needle before and after use, said sheath comprising a tubular element sized to enclose said needle and having a wall adapted to be grasped by fingers at a locus midway along its length for withdrawal and insertion of said needle, and a disc element mounted transversely on said sheath tubular element above said locus, said disc element being resistant to needle penetration and projecting laterally of said sheath tubular element a distance to clock said syringe needle from reaching said fingers gripping said sheath tubular element below said disc, said disc element defining an over-center structure adapted to snap between said parallel and transverse positions relative to said sheath tubular element responsive to flexing of the sheath tubular element wall below said disc element.

2. Safety needle containment according to claim 1, in which said sheath tubular element comprises rigid synthetic organic plastic.

3. Safety needle containment according to claim 1, in which said disc element comprises rigid synthetic organic plastic.

4. Safety needle containment according to claim 1, including also cooperating structure on said needle structure hub and said sheath tubular element for removably interfitting said hub and said sheath tubular element in needle enclosing relation.

5. Safety needle containment according to claim 1, in which said disc element is locally flexible adjacent said sheath tubular element for alignment transverse to or parallel with said sheath tubular element wall between protective and storage positions respectively.

6. Safety needle containment according to claim 5, in which said disc element is centrally apertured and fixed to said sheath tubular element wall at its said central aperture.

7. Safety needle containment according to claim 6, in which said disc element is integrally formed with said sheath tubular element wall.

8. Safety needle containment according to claim 6, in which said sheath tubular element comprises rigid synthetic organic plastic, and said needle structure comprises a hub having a first needle extending from one side and a second needle extending from the opposite side, said hub being adapted to snugly interfit with said sheath tubular element, and including also a cap adapted to completely enclose said needle structure in cooperation with said sheath.

9. Safety needle containment according to claim 8, in which said disc element comprises rigid synthetic organic plastic.

10. Safety needle containment according to claim 9, in which said needle structure hub is internally threaded for mounting a medicament supply to said needle structure.

11. In combination: a syringe comprising a rigid plastic barrel having a plunger and a needle outlet arranged for delivery of medicament; a needle structure including a first needle for administering medicament and a second needle for piercing said syringe barrel needle outlet, said first and second needles extending oppositely from a common hub; and a sheath forming a needle protective enclosure, said sheath having a disc element flange formed thereon to deflect said first needle from fingers gripping said sheath during insertion of said first needle into said sheath.

12. Safety needle containment according to claim 11, in which said disc element is coupled to said sheath in a manner to flex into and out of more relatively parallel alignment with said sheath responsive to lateral flexing of said sheath for storage or protective deployment respectively of said disc element.

* * * * *